United States Patent [19]

Graziano

[11] 4,266,298
[45] May 12, 1981

[54] INFLATABLE HEEL PROTECTOR

[75] Inventor: Joseph L. Graziano, Oak Park, Ill.

[73] Assignee: Marlene S. Mindey, Chicago, Ill.

[21] Appl. No.: 117,373

[22] Filed: Jan. 31, 1980

[51] Int. Cl.³ ............................................. A41D 13/06
[52] U.S. Cl. .................................... 2/22; 36/71; 128/89 R
[58] Field of Search .............. 2/22, 24, 2, DIG. 6; 36/71; 128/89 R, 85, 87 R

[56] References Cited

U.S. PATENT DOCUMENTS

| | | | |
|---|---|---|---|
| 3,561,435 | 2/1971 | Nicholson | 128/87 R X |
| 3,804,085 | 4/1974 | Eshuis et al. | 128/85 |
| 3,854,228 | 12/1974 | Conroy | 36/71 |
| 3,877,077 | 4/1975 | Chapdelaine | 2/22 |

FOREIGN PATENT DOCUMENTS

| | | | |
|---|---|---|---|
| 18732 | of 1893 | United Kingdom | 2/22 |
| 2016905 | 9/1979 | United Kingdom | 2/22 |

*Primary Examiner*—H. Hampton Hunter
*Attorney, Agent, or Firm*—Dressler, Goldsmith, Shore, Sutker & Milnamow, Ltd.

[57] ABSTRACT

An inflatable heel protector for cushioning a foot is provided which comprises an inflatable bag formed by joining a first flexible wall and second flexible wall along their respective peripheral edges. The first and second walls are also joined to form interconnecting pillow segments so that fluid can flow between the segments to distribute pressure imparted to the bag. Releasable coacting fastening tabs are provided to hold the bag in place on the lower leg, and a reclosable valve on the bag enables fluid insertion or removal.

14 Claims, 3 Drawing Figures

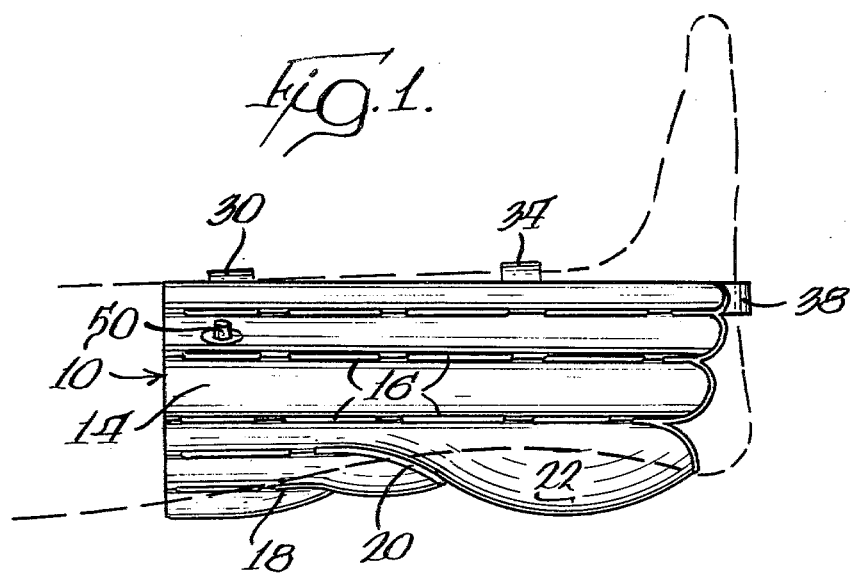
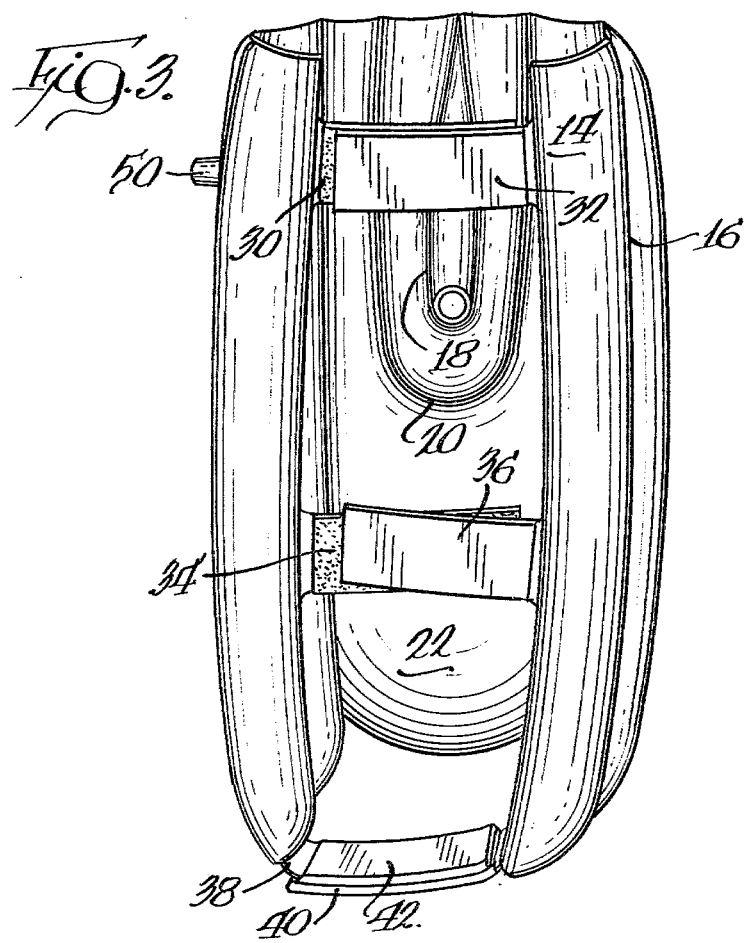

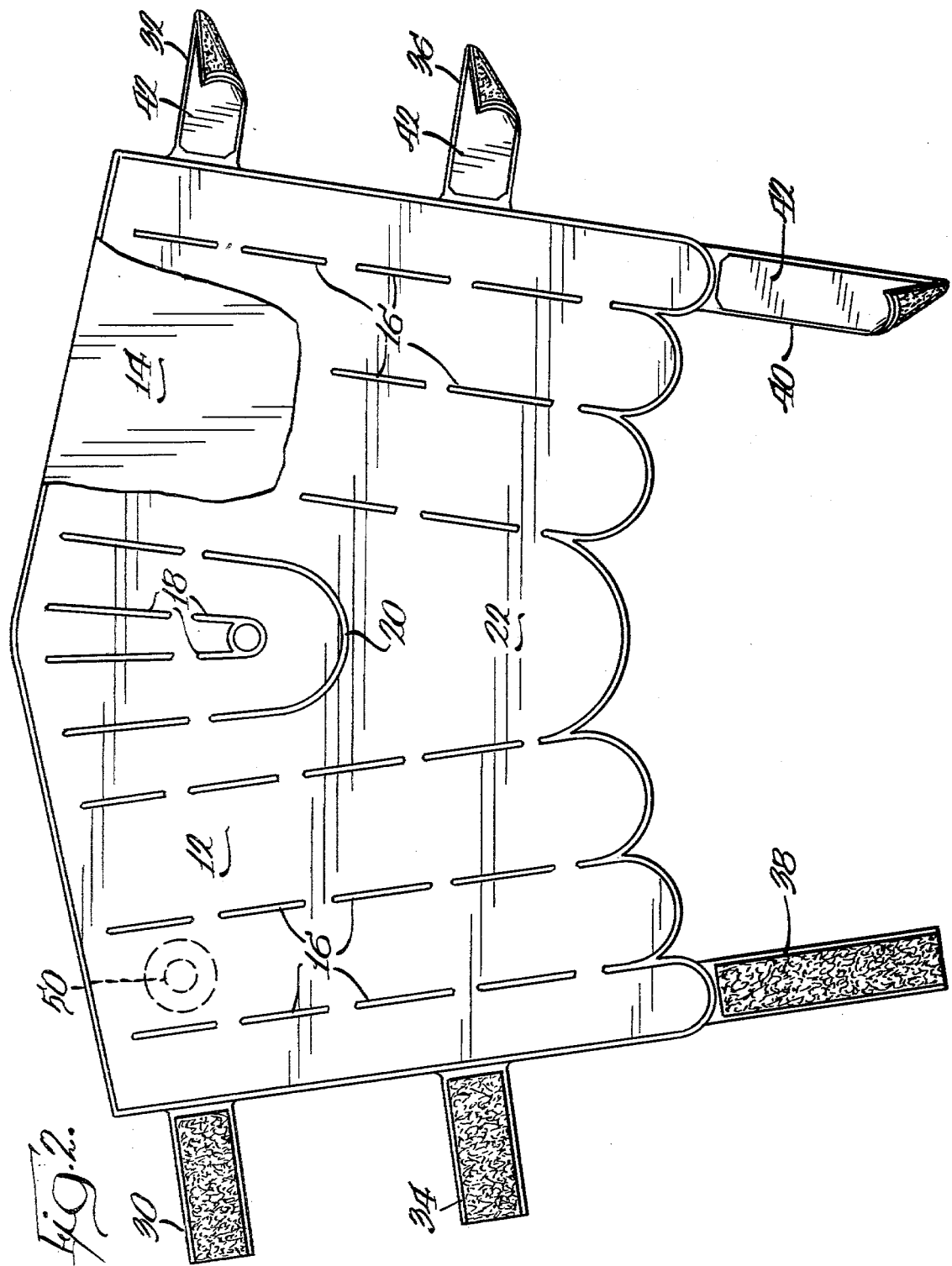

INFLATABLE HEEL PROTECTOR

TECHNICAL FIELD

This invention relates to leg protectors and more particularly to an apparatus to support and protect sensitive or diseased heels of elderly and/or debilitated patients.

BACKGROUND OF THE INVENTION

Recently, an increasing number of elderly patients are being cared for in hospitals, extended care facilities and nursing homes. Many of these patients are bedridden or spend most of their time in bed. Decubitus ulcers are commonly seen in bedridden, elderly and/or debilitated patients, and the heel area is the most common place on a patient for tissue to break down.

Presently available heel protectors have not proven to offer sufficient protection to the sensitive areas. Cloth heel protectors, with insulated padding, are among the prior attempts to deal with this problem. However, such a protector does not adequately distribute forces imparted to the foot over more of the foot area to thereby decrease the pressure on the sensitive areas.

Also, the presently available heel protectors have failed to provide a means for being adequately fastened to the foot and ankle. A common occurrence is for the heel protectors to slide upwards along the lower leg. Also, the presently available means to fasten these heel protectors to the foot and ankle have been known to irritate the skin of the patient and/or require considerable effort to put on and remove.

SUMMARY OF THE INVENTION

In accordance with the present invention, an inflatable heel protector for cushioning a foot is provided comprising an inflatable bag formed by joining a first flexible wall and second flexible wall along their respective peripheral edges. The exterior surface of the first wall contacts the foot and is separated from the second wall by a cushion of fluid over most of the interior surface of the bag, with portions of the interior of the first wall being joined to corresponding portions of the interior of the second wall to form interconnecting pillow segments. Fluid in any particular pillow segment can thus communicate with fluid in other pillow segments, and the ribs help the protector conform to the lower leg and distribute forces more evenly. Releasable padded fastening means are also provided to fasten the protector to the lower leg to keep it from sliding along the lower leg of the patient.

Thus, pressure applied to the exterior second wall is distributed more uniformly over the first wall which contacts the foot. The pressure distribution can be adjusted by varying the amount of fluid inserted in the bag through a reclosable valve means. The releasable fastening means are padded to cushion the foot, are easily engaged and released, and are placed so that the protector does not slide with respect to the foot and retains its position thereon.

BRIEF DESCRIPTION OF THE DRAWING

In the accompanying drawing,

FIG. 1 is an illustration of the inflatable heel protector of the present invention shown fitted on a patient's lower leg, FIG. 2 is an illustration of the inflatable heel protector shown deflated and flat in partial cross-section; and FIG. 3 is an illustration of the inflatable heel protector shown from the front view with all of the fastening tabs engaged, and showing the channel wherein a foot and lower leg can be received.

DESCRIPTION OF THE PREFERRED EMBODIMENT

Referring to the drawing, an inflatable bag 10 is shown comprised of two overlapping, generally equally sized first flexible wall 12 and second flexible wall 14. The exterior surface of the first wall 12 is intended to contact the foot and lower leg when the heel protector is worn by a patient. The first wall 12 and second wall 14 are joined together generally along their respective peripheral edges.

Besides being joined along their respective edges, portions of the interior of the first wall 12 are joined to corresponding portions of the interior of the second wall 14 to form interconnecting pillow segments of varying sizes and shapes. The pillow segments are interconnected so that fluid in any one pillow segment can communicate with fluid in its immediately adjacent pillow segment. This serves to distribute forces imparted on the exterior of the second wall over a wider area on the first wall when the heel protector is worn by a patient.

Along the side edges of the bag, the first wall and second wall are joined so as to form generally linear ribs 16. This linear rib configuration enables the protector to bend to form a generally U-shaped channel to receive and conform to the sides of the leg when the protector is worn by a patient.

In the middle area of the bag, the first wall and second wall are joined so as to form two generally concentric U-shaped ribs 18 and 20. This enables the protector to fit and conform to the back of the lower leg and aids in more evenly distributing the forces imparted to the bag over the lower foot area when the bag is worn by a patient.

The placement of U-shaped rib 20 is such that a relatively large pillow segment is defined immediately below it as designated by reference numeral 22. As shown in FIG. 1, this pillow segment 22 extends more rearwardly from the lower leg than the base of the heel of a patient so that when the patient is in a horizontal position on his back this particular segment will receive most of the counteracting forces caused by the weight of the lower leg.

The bag is provided with a means to fasten the protector to the lower leg. This fastening arrangement comprises pairs of coacting releasable fastening tabs, each tab of a pair being attached to and extending from an opposing peripheral edge of the bag from its other tab in the pair when the protector is in contact with the foot. Thus, fastening tab 30 extends from the peripheral edge of the side of the bag and coacts with fastening tab 32 extending from the opposing peripheral edge of the side of the bag. Velcro, or other suitable coacting and mating releasable fastening material, is firmly affixed to the tabs 30 and 32 so that when the bag is fitted to the leg and when fastening tab 30 is overlayed upon fastening tab 32, the bag is held firmly in place.

Fastening tab 34 and fastening tab 36 are also disposed to each other similar to fastening tabs 30 and 32 and also contain suitable coacting releasable fastening material such as Velcro. Fastening tabs 34 and 36 are positioned on the sides of the bag 10 so that when the bag is formed in a U-shaped arrangement around the leg, and pillow segment 22 is received in the hollow portion of the leg, the pair of tabs 34 and 36 hold the pillow segment 22 in the hollow portion of the back of the leg.

Fastening tabs 38 and 40 are also positioned on the peripheral edges of the bag so that when the protector is in contact with the foot, each tab extends from an opposing peripheral edge of the bag, as shown in FIG. 3. Tabs 38 and 40 also contain suitable coacting releasable fastening material. Thus, the fastening tabs 38 and 40, when fastened to each other, form a stirrup to hold the protector in place on the lower leg of a patient and keep it from sliding upwards on the leg.

The fastening tab of each pair that contacts the patient's skin has attached to it a padded cushion strip 42, so that when this tab contacts the skin, the strip 42 will cushion the skin from being irritated.

Preferably, the bag 10 is generally chevron in shape so that when the bag is fitted to the back of the lower leg, the lower peripheral edge of the bag at the base of pillow segment 22 is above the base of the rear of the heel, as shown in FIG. 1, whereas the lower peripheral edges of the bag 10 at the sides of the foot extend generally to the base of the foot so that the stirrup fastening tabs 38 and 40 will be placed to be most comfortable to the patient.

The inflatable heel protector is also provided with a reclosable valve 50, which provides a means to insert and remove fluid such as air under pressure into and from the bag. Thus, the bag can be stored and packaged in a deflated condition and can be inflated when about to be worn. Also, by adjusting the amount of fluid inside the bag 10, the degree with which the bag distributes forces exerted on the exterior of the second wall over the area on the first wall can be adjusted. Further, when the bag might lose fluid due to small leaks, fluid that has been lost can be periodically replaced.

The invention is suited to be worn by a wide variety of patients, since the amount of fluid in the bag can be adjusted to achieve the desired results on different sizes of feet. The respective fastening tab pairs also provide for fitting the protector to different sizes of feet.

Preferably, the reclosable valve 50 is located on the exterior surface of the second wall on a side pillow segment, so that when the bag is worn, the valve will be located more towards the frontal area of the leg than the side area of the leg. Thus, when the patient rolls his leg on the bed, the valve stem will not otherwise cause discomfort to his leg by jabbing him.

While this reclosable valve means is provided, it can be appreciated that the bag can be manufactured fully sealed with fluid already contained therein without such a valve means, and still perform the same function of cushioning the foot and protecting the heel.

The inflatable heel protector of the present invention is adapted to be used by a large number of patients, and can be worn by either a left or right foot, since it is generally symmetrical.

From the foregoing, it will be observed that numerous variations and modifications may be effected without departing from the true spirit and scope of the novel concept of the invention. It is to be understood that no limitation with respect to specific apparatus illustrated herein is intended or should be inferred. It is, of course, intended to cover by the appended claims all such modifications as fall within the scope of the claims.

What is claimed is:

1. A heel protector for cushioning a foot comprising:
a first wall adapted to contact a foot;
a second wall joined with said first wall generally along its respective peripheral edge to form a bag, said first and second walls being adapted to distribute the forces exerted on the second wall over a larger area of the first wall and said second wall being separated from said first wall by a cushion of fluid along most of its interior surface, means joining portions of the interior of the first wall to corresponding portions of the interior of the second wall to form interconnecting pillow segments, so that fluid in any pillow segment can communicate with fluid in other pillow segments, to further aid in the distribution of forces exerted on the second wall over a wider area on the first wall; and
means to fasten said protector in a generally U-shaped arrangement where it can function to protect that which it surrounds against damage.

2. The heel protector of claim 1 wherein a reclosable valve means is attached to said bag for inserting and removing fluid into and from the bag.

3. The heel protector of claim 1 wherein said fastening means comprises at least one pair of coacting releasable fastening tabs, each tab being attached to and extending from an opposing peripheral edge of the bag from its associated tab in the pair, when the protector is in contact with the foot.

4. The heel protector of claim 1 wherein the first wall and second wall are joined so as to form generally linear ribs where the protector fits the sides of a lower leg so that the protector can bend to form a channel to receive and conform to the rear and sides of the lower leg.

5. The heel protector of claim 1 wherein the first wall and second wall are joined so as to form at least one U-shaped rib where a protector may be adapted to fit the back of the lower leg so that the bag conforms to the lower leg and aids in more evenly distributing the forces imparted to the bag over the lower foot area.

6. The heel protector of claim 1 wherein the bag is generally chevron in shape so that when the bag is fitted to the back of a lower leg, the lower peripheral edge of the bag stops short from the base of the foot, but that the lower peripheral edge of the bag at the sides of the foot extends to the base of the foot.

7. The heel protector of claim 1 wherein said fluid is air.

8. A heel protector for cushioning a foot comprising:
an interior first wall to contact the foot;
an exterior second wall joined with said first wall generally along the peripheral edges of said walls to form a bag, said first and second walls being adapted to distribute the forces exerted on the second wall over a large area of the first wall and said second wall being separated from said first wall by a cushion of fluid along most of its interior surface, and wherein portions of the interior of the first wall are joined to corresponding portions of the interior of the second wall to form generally linear ribs where the protector fits the sides of the lower leg, and wherein the interior surfaces of the walls are joined to form at least one U-shaped rib where the protector fits the back of the lower leg, forming interconnected pillow segments so that fluid in any pillow segment can communicate with fluid in adjacent pillow segments to further aid in the distribution of forces exerted on the second wall over a wider area on the first wall;

a reclosable valve means for inserting and removing fluid into and from the bag; and fastening means to fasten said protector in a generally U-shaped arrangement where it can function to protect the foot and heel against damage.

9. The heel protector of claim 8 wherein the fastening means comprises at least one pair of coacting releasable fastening tabs, each tab being attached to and extending from an opposing peripheral edge of the bag from its associated tab in the pair when the protector is in contact with the foot.

10. The heel protector of claim 9 wherein at least one tab of each fastening tab pair has a padded cushion strip where the tab contacts the skin when the protector is worn.

11. The heel protector of claim 9 wherein one pair of fastening tabs are located approximately midway up the sides of the frontmost pillow segments when the bag is fitted to the foot.

12. The heel protector of claim 9 wherein one tab of each fastening tab pair is located generally at the bottom edge of the frontmost pillow segment of each side so that the tabs, when fastened, form a stirrup to hold the protector in place on the lower leg.

13. The heel protector of claim 8 wherein the reclosable valve means is located on the upper region of the exterior surface of the second wall on a frontmost pillow segment.

14. The heel protector of claim 8 wherein said fluid is air.

* * * * *

REEXAMINATION CERTIFICATE (2885th)

United States Patent [19]
Graziano

[11] B1 4,266,298
[45] Certificate Issued May 21, 1996

[54] INFLATABLE HEEL PROTECTOR

[75] Inventor: Joseph L. Graziano, Chicago, Ill.

[73] Assignee: Marlene S. Mindey, St. Thomas, Virgin Islands (U.S.)

Reexamination Request:
No. 90/003,777, Apr. 3, 1995

Reexamination Certificate for:
Patent No.: 4,266,298
Issued: May 12, 1981
Appl. No.: 117,373
Filed: Jan. 31, 1980

[51] Int. Cl.$^6$ ............................................ A41D 13/06
[52] U.S. Cl. ........................... 2/22; 2/910; 36/71; 5/457; 5/650; 602/13
[58] Field of Search ............... 2/22, 23, 24; 602/26, 602/27, 62, 63, 65

[56] References Cited

U.S. PATENT DOCUMENTS

| | | |
|---|---|---|
| 1,726,939 | 9/1929 | Anderson. |
| 2,267,070 | 12/1940 | Baldwin. |
| 2,651,302 | 9/1953 | Berry. |
| 3,164,152 | 1/1965 | Nicoll. |
| 3,338,237 | 8/1967 | Sconce. |
| 3,561,435 | 2/1971 | Nicholson ..................... 128/87 R X |
| 3,668,704 | 1/1974 | Conroy et al.. |
| 3,685,176 | 8/1972 | Rudy. |
| 3,758,964 | 9/1973 | Nishimura. |
| 3,771,519 | 11/1973 | Haake. |
| 3,804,085 | 4/1974 | Eshuis et al. ..................... 128/85 |
| 3,854,228 | 12/1974 | Conroy ............................ 36/71 |
| 3,877,077 | 4/1975 | Chapdolaine ..................... 2/22 |
| 4,157,713 | 6/1979 | Clarey. |
| 4,197,845 | 4/1980 | Browning. |
| 4,226,298 | 5/1981 | Graziano. |

FOREIGN PATENT DOCUMENTS

| | | |
|---|---|---|
| 440113 | 1/1927 | Germany. |
| 1873208 | of 1893 | United Kingdom ............... 2/22 |
| 18732 | of 1894 | United Kingdom. |
| 1171361 | 6/1967 | United Kingdom. |
| 2016905 | 9/1979 | United Kingdom ............... 2/22 |

*Primary Examiner*—Paul C. Lewis

[57] ABSTRACT

An inflatable heel protector for cushioning a foot is provided which comprises an inflatable bag formed by joining a first flexible wall and second flexible wall along their respective peripheral edges. The first and second walls are also joined to form interconnecting pillow segments so that fluid can flow between the segments to distribute pressure imparted to the bag. Releasable coacting fastening tabs are provided to hold the bag in place on the lower leg, and a reclosable valve on the bag enables fluid insertion or removal.

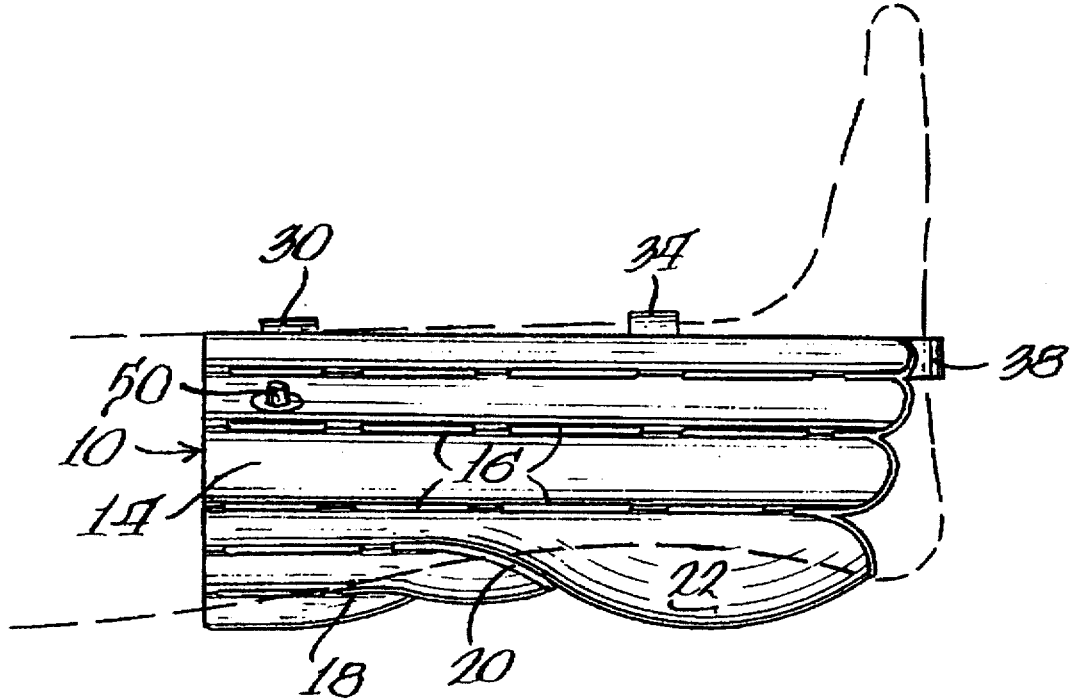

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–14 are cancelled.

* * * * *